United States Patent [19]

Gorny et al.

[11] 4,330,323
[45] May 18, 1982

[54] DICHLOROACETAMIDE AND TRICHLOROACETAMIDE DERIVATIVES WHICH ARE ANTIDOTES AGAINST HERBICIDES

[75] Inventors: Bernard S. J. M. Gorny, Eybens; Jean-Paul Brun, Echirolles; Gérard E. M. Boutemy, Milly La Foret; Michel L. Devif, Chailly en Biere, all of France

[73] Assignee: PCUK Produits Chimiques Ugine Kuhlmann, Courbevoie, France

[21] Appl. No.: 42,478

[22] Filed: May 25, 1979

Related U.S. Application Data

[63] Continuation of Ser. No. 930,086, Aug. 1, 1978, abandoned.

[30] Foreign Application Priority Data

Aug. 3, 1977 [FR] France .................................. 77 23866

[51] Int. Cl.³ ..................... A01N 37/00; A01N 43/48; A01N 43/64
[52] U.S. Cl. .......................................... 71/100; 71/88; 71/92; 71/93; 71/110; 71/111; 71/118; 71/120; 564/152; 564/155; 564/158; 564/159; 564/209; 260/404
[58] Field of Search ............ 260/561 HL, 557 R, 404, 260/558 R, 562 B; 544/400; 71/118, 110, 100, 111, 120, 93, 92

[56] References Cited

U.S. PATENT DOCUMENTS

| | | | |
|---|---|---|---|
| 2,742,501 | 4/1956 | Kleing et al. ........................ | 260/562 |
| 3,525,744 | 8/1972 | Fest et al. ..................... | 260/561 HL |
| 3,707,477 | 12/1972 | Ost et al. .............................. | 544/400 |
| 3,923,494 | 12/1975 | Teach ..................................... | 71/88 |
| 4,146,646 | 3/1979 | Percival et al. ....................... | 424/324 |

FOREIGN PATENT DOCUMENTS

| | | |
|---|---|---|
| 1186467 | 2/1965 | Fed. Rep. of Germany . |
| 1617457 | 4/1971 | Fed. Rep. of Germany . |
| 2047258 | 10/1971 | Fed. Rep. of Germany . |
| 2358592 | 5/1975 | Fed. Rep. of Germany . |
| 105113 | 4/1974 | German Democratic Rep. . |

OTHER PUBLICATIONS

Melnikov et al., Chemistry of Pesticides; Springer-Verlog, N. Y. N. Y., 1971, p. 1–6.
Carter et al., Chem. Abst. 80 (1974) #116992.
Brown et al., Chem. Abst. 84 (1976) #85400 and #85401.
Kashik et al., Chem. Abst. (1971) #151233.
Wagner et al., Synthetic Organic Chemistry, John Wiley & Sons, N. Y. N. Y., 1953 pp. 566, 665, 666.

*Primary Examiner*—Arthur P. Demers
*Attorney, Agent, or Firm*—Beveridge, Degrandi and Kline

[57] ABSTRACT

The compounds of the formula:

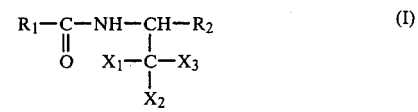

in which $R_1$ represents a dichloromethyl or trichloromethyl group, $X_1$ represents a chlorine or fluorine atom, $X_2$ represents a chlorine or fluorine atom, $X_3$ represents a hydrogen, chlorine or fluorine atom, $R_2$ represents an amino group $NH_2$ or a

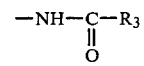

group, in which $R_3$ represents a hydrogen atom or an alkyl, haloalkyl, alkenyl, haloalkenyl, arylalkyl, arylhaloalkyl, cycloalkyl, halocycloalkyl, alkoxyalkyl, haloalkoxyalkyl or aryl group, this latter being unsubstituted or substituted by one or two halogen atoms or by an alkyl, alkoxy, nitro or haloalkyl group are antidotes against herbicides.

6 Claims, No Drawings

DICHLOROACETAMIDE AND TRICHLOROACETAMIDE DERIVATIVES WHICH ARE ANTIDOTES AGAINST HERBICIDES

This is a continuation of application Ser. No. 930,086, filed Aug. 1, 1978 now abandoned.

BACKGROUND OF THE INVENTION

1. Field of the Invention

The present invention relates to new dichloroacetamide and trichloroacetamide derivatives, processes for their preparation and their application as antidotes against herbicides.

2. Description of the Prior Art

Herbicides existing at the present time may be classed in two categories: total herbicides, which destroy all plants, and selective herbicides. The latter, which are the most valuable in agriculture, enable the weeds present in croplands to be destroyed without harming the cultivated plant and for this reason are said to be selective for the cultivated plant. Unfortunately, it often occurs that this selectivity may not be perfect at the dose used and that the selective herbicides show some phytotoxicity towards the cultivated plant.

There may also be used, in association with herbicides, products said to be antidotes against herbicides which have the property of imparting to the herbicides an increased selectivity or new selectivities, without being prejudicial to their herbicidal quality. In other words, the antidote makes the phytotoxicity of the herbicide towards the cultivated plant disappear entirely or at least to a great extent without reducing its phytotoxicity towards unwanted plants.

Such antidotes against herbicides have been described, for example in French Pat. No. 2,133,793, corresponding at least in part to U.S. Pat. Nos. 4,137,070, 2,212,336, corresponding at least in part to U.S. Pat. Nos. 3,989,503, 2,215,170, 2,228,065, 2,309,546 corresponding at least in part to U.S. Pat. Nos. 4,072,688 and 2,310,348, and in U.S. Pat. Nos. 3,867,444, 3,923,494, 3,931,313 and 3,959,304.

The object of the present invention is to obtain chemically new compounds which are themselves active as antidotes against herbicides.

SUMMARY OF THE INVENTION

The compounds according to the invention may be represented by the general formula:

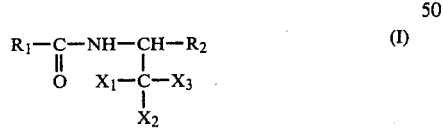 (I)

in which $R_1$ represents a dichloromethyl or trichloromethyl group, $X_1$ represents a chlorine or fluorine atom, $X_2$ represents a chlorine or fluorine atom, $X_3$ represents a hydrogen, chlorine or fluorine atom, $R_2$ represents an $NH_2$ amino group or a

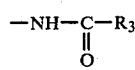

group in which $R_3$ is a hydrogen atom or an alkyl, haloalkyl, alkenyl, haloalkenyl, arylalkyl, arylhaloalkyl, cycloalkyl, halocycloalkyl, alkoxyalkyl, haloalkoxyalkyl or aryl group, the latter being unsubstituted or substituted by one or two halogen atoms or by an alkyl, alkoxy, nitro or haloalkyl group.

In the definitions given above for $R_3$, the alkyl, alkenyl, and alkoxy chains of the alkyl, haloalkyl, alkenyl, haloalkenyl, arylalkyl, arylhaloalkyl, alkoxyalkyl and haloalkoxyalkyl groups preferably have 1 to 5 carbon atoms, the cycloalkyl and halocycloalkyl groups preferably have 3 to 6 carbon atoms, the haloalkyl, haloalkenyl, arylhaloalkyl, halocycloalkyl and haloalkoxyalkyl groups preferably have 1 to 7 halogen atoms which may be chlorine, bromine or fluorine, the aryl group preferably denotes phenyl, and the halogen substituent of the aryl group is preferably a chlorine atom.

DESCRIPTION OF THE PREFERRED EMBODIMENTS

While the present invention relates broadly to the compounds of formula (I), it is more particularly directed to those compounds wherein $R_2$ is $NH_2$ or

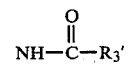

group in which $R_3'$ is a hydrogen atom, an alkyl group having 1 to 5 carbon atoms, an alkenyl group having 2 to 5 carbon atoms, a haloalkyl group having 1 to 5 carbon atoms and 1 to 7 halogen atoms, or a phenyl group substituted by one or two chlorine atoms. When $R_3'$ is a haloalkyl group, it is preferably a

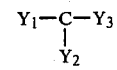

group wherein $Y_1$ is a chlorine or fluorine atom, $Y_2$ is a chlorine or fluorine atom and $Y_3$ is a hydrogen, chlorine or fluorine atom.

The compounds of formula (I) for which $R_2$ is a

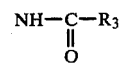

group may be prepared by several methods, namely:

(1) the action of an acid chloride of the formula

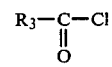

on an amino compound of formula (II) below according to the reaction:

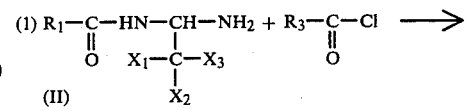

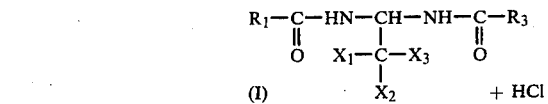

(2) the action of an acid chloride of the formula

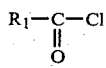

on an amino compound of formula (III) below according to reaction:

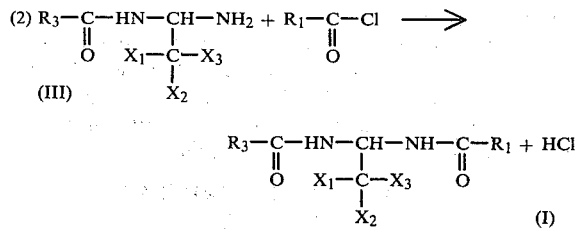

(3) the action of an amide of the formula

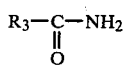

on a chlorinated derivative of formula (IV) below according to the reaction:

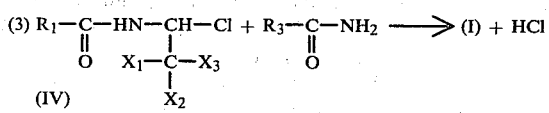

(4) the action of an amide of the formula

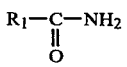

on a derivative of formula (V) below according to the reaction:

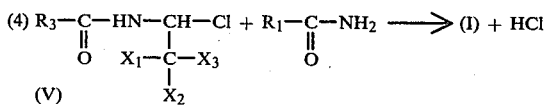

In the formulae (II), (III), (IV) and (V) above as well as in those of the acid chlorides and amides, $X_1$, $X_2$, $X_3$, $R_1$ and $R_3$ have the same significance as in formula (I).

The reactions (1), (2), (3) and (4) are effected preferably in an inert solvent such as, for example, a linear or cyclic ether, an aliphatic or aromatic hydrocarbon or a chlorinated derivative of an aliphatic or aromatic hydrocarbon, at a temperature between $-30°$ C. and $+60°$ C. and preferably between $-15°$ C. and $+30°$ C. The hydrochloric acid formed in the reaction is neutralized as it is formed by a mineral base such as, for example, an alkali or alkaline earth metal hydroxide or by a tertiary amine such as triethylamine or pyridine. After separation of the chloride of the mineral base or of the hydrochloride of the amine by extraction with water or by filtration, the product of formula (I) formed is isolated in the crude state by removal of the solvent by distillation. It may be purified, for example by recrystallization, or used as such.

The compounds of formula (I) in which $R_2$ is an $NH_2$ group, which are identical with the compounds of formula (II), and the compounds of formula (III) may be prepared by the action of ammonia on the chlorinated derivatives of formulae (IV) and (V). The reaction is carried out in the same solvents as those used for reactions (1) to (4) and preferably in a cyclic ether such as, for example, tetrahydrofuran. The chlorinated derivative of formula (IV) or (V) is introduced into the solvent saturated with ammonia, at a temperature between $-30°$ C. and $+30°$ C. The ammonium chloride formed is removed by filtration and the compound of formula (II) or (III) is isolated in the crude state by elimination of the solvent. It may be purified by recrystallization or used as such, particularly for effecting the reactions (1) or (2).

The compounds of formulae (IV) and (V) may be prepared by the action of thionyl chloride on the hydroxy compounds of the formulae:

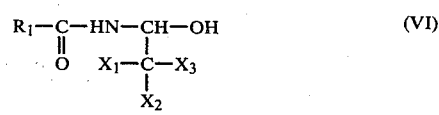

and

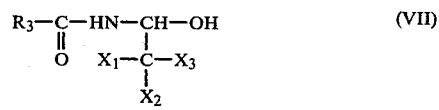

in which $R_1$, $R_3$, $X_1$, $X_2$, $X_3$ have the same significance as in formula (I). The reaction may be carried out, in the presence or absence of a solvent, with an excess of thionyl chloride, at a temperature between $50°$ C. and $80°$ C. The solvent used may be the same as those used to effect reactions (1) to (4). When a solvent is not used, and also when certain solvents such as, for example, $CCl_4$ or hexane are used, the compound of formula (IV) or (V) is precipitated and may be isolated by filtration. When other solvents are used as, for example, tetrahydrofuran, the compound of formula (IV) or (V) is not precipitated. The product may then be isolated by evaporation of the solvent under vacuum, or the medium obtained at the end of the reaction may be used directly for the continuation of the process leading to the compounds (I), without isolating the products (IV) or (V).

The hydroxy compounds of formulae (VI) or (VII) may be prepared by the action of an amide of the formula

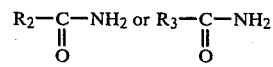

on a halogenated aldehyde of the formula:

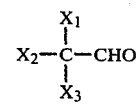

according to the processes described by Joseph P. Larocca, John M. Leonard, Warren EF. Weaver [Journal of Organic Chemistry 16, 47–50, (1951)] and by A. Boucherle, G. Carraz, J. Vigier [Bull. Trav. Soc. Pharm. Lyon 10 (1), 3–10, (1966)].

The compounds of formula (III) for which $R_3$ is not a hydrogen atom are new and as such form part of the present invention. As examples of new compounds of formula (III) may be particularly mentioned those for which simultaneously $X_1=X_2=X_3=Cl$ and $R_3$=monochloromethyl, trichloromethyl, 1,2,3,3,3-pentachloropropyl, trifluoromethyl, methyl, o-chlorophenyl, p-chlorophenyl, p-methylphenyl, m-trifluoromethylphenyl, 2,4-dichloro-phenyl or 3,4-dichloro-phenyl.

Some of the compounds of formulae (IV), (V), (VI), (VII) are also new products. As such may be mentioned in particular the compounds corresponding to the formula:

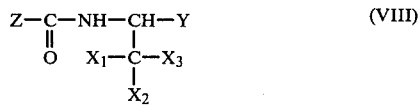

in which $X_1$, $X_2$, $X_3$ have the same significance as in formula (I), Y is a chlorine atom or a hydroxy group, Z is an n-heptyl, n-nonyl, trifluoromethyl, 1,2,3,3,3-pentachloropropyl, p-methylphenyl or m-trifluoromethylphenyl group and may be further, when $X_1$, $X_2$, $X_3$ are not simultaneously chlorine atoms, a dichloromethyl group.

The compounds of formula (I) may be used, as antidotes against herbicides, for the treatment of crops and croplands. They protect the cultivated plants against the damage occasioned by the herbicides at doses of the herbicides which are effective against undesired plants.

The compounds of formula (I) may be employed especially in association with herbicides belonging to the families of chloroacetanilides, ureas, triazines, carbamates, uracils and more especially, thiolcarbamates. Examples of such herbicides include ethyl N,N-dipropyl-thiolcarbamate (EPTC), ethyl N,N-diisobutyl-thiolcarbamate (butylate), propyl N,N-dipropylthiolcarbamate, ethyl N,N-diethyl-thiolcarbamate (ethiolate), ethyl N,N-cyclohexamethylene thiolcarbamate (molinate), ethyl N-ethyl-N-cyclohexyl-triolcarbamate (cycloate), 2,3 dichloropropenyl N,N-diisopropyl-thiolcarbamate (diallate), ethyl N,N-diisopropyl-thiolcarbamate, 4-chloro-2-butynyl-N-(3-chlorophenyl)-carbamate (barban), 3-(3-chloro-4-methyl-phenyl)-1-1-dimethyl-urea (chlortoluron), 3-(3,4-dichloro-phenyl)-1-methoxy-1-methyl-urea (linuron), 3-(3,4-dichloro-phenyl)-1,1-dimethylurea, N-chloroacetyl-N-isopropyl-aniline (propachlor), 2,6-diethyl-N-chloroacetyl N-methoxymethyl-aniline (alachlor), 2-chloro-4-ethylamino-6-isopropylamino-1,3,5-triazine (atrazine), 2-chloro-bis-4,6-(ethylamino)-1,3,5-triazine, 2-chloro-4-cyclopropylamino-6-isopropylamino-1,3,5-triazine and their combinations. The weight ratio $$\frac{\text{antidote product}}{\text{herbicide}}$$

to be used may vary greatly according to the nature of the herbicide concerned. This ratio is generally between 0.001 and 10, and most often between 0.01 and 5.

For their use, the compounds of formula (I) may be incorporated, jointly with the herbicide or separately, in compositions which contain in addition to the active material (that is, the antidote compound and possibly the herbicide), inert additives commonly used in agriculture to facilitate the conservation, application and penetration into the plants of the active products, such as mineral charges (talc, silica, kieselguhr, diatomaceous earths, clay, etc.), various organic diluents (mineral oils, organic solvents), surface-active substances, antioxidants and stabilizers. Such compositions may be present in the form of wettable powders, solutions emulsifiable in water, granules or any other form in use in the herbicidal field. In compositions containing only an antidote compound according to the invention and inert additives, the content of antidote compound may vary from 10% to 90% by weight. In compositions containing an antidote compound according to the invention, a herbicide and inert additives, the content of antidote compound may vary from 0.09% to 50% by weight, and that of herbicide from 1% to 90% by weight, the ratio $$\frac{\text{antidote product}}{\text{herbicide}}$$

by weight being between 0.001 and 10.

The antidote compounds according to the invention may be applied to the soil at the same time as the herbicide, in preemergence or post-emergence stages of the cultivated plants. The dose of antidote used may vary from 100 g to 5000 g per hectare. For such an application it is advantageous to use compositions containing simultaneously the antidote and the herbicide, such as those previously mentioned.

The antidote compounds according to the invention may also be applied to the soil at a different time from that of the treatment with herbicide, in pre-emergence or post-emergence stages of the cultivated plants, the dose of antidote used being the same as above. In particular, they may be applied to soils containing herbicidal residues in order to protect the cultivated plants against the remaining activity of these residues.

Finally, the antidote compounds according to the invention may also be applied to the seed of the cultivated plant to be protected, said seed then being sown in soil already treated with the herbicide or which will be treated with the herbicide. For treatment of the seeds, the dose of antidote used may vary from 10 g to 500 g per hundredweight of seed.

The following examples illustrate the invention without restricting it thereto. In the examples and throughout the specification and claims, all parts and percentages are by weight unless otherwise specified.

EXAMPLE 1

Preparation of the compound of the formula:

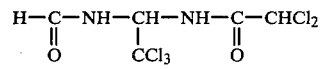

19.15 g (0.1 mole) of N-[(2,2,2-trichloro-1-amino)-ethyl]formamide are dissolved in 200 ml of tetrahydrofuran (THF). 10.1 g of triethylamine (0.1 mole) are added. While the temperature is maintained at 15° C., 14.75 g of dichloroacetyl chloride (0.1 mole) dissolved in 100 ml of THF are added with stirring in about 30 minutes. Stirring is then continued for one-half hour while the temperature is allowed to return to the ambient temperature. The precpitate of triethylamine hydrochloride is filtered off and the THF is eliminated by distillation in vacuum. During the distillation, a crystalline product is formed which is separated. This product is recrystallized from a 50—50 benzene-hexane mixture. 24.5 g (a yield of 81%) of N-[(2,2,2-trichloro-1-dichloroacetamido)ethyl]-formamide having a melting point of 141°-142° C. are thus obtained.

EXAMPLE 2

Preparation of the compound of the formula:

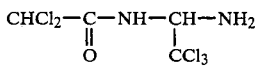

300 ml of tetrahydrofuran are saturated with gaseous ammonia and this saturation is maintained during the entire operation. While keeping the temperature at −5° C., 150 g (0.5 mole) of N-[(1,2,2,2-tetrachloro)-ethyl]-dichloroacetamide are added while stirring in a period of about 1 hour and 30 minutes. A precipitate of ammonium chloride is formed during the addition, and this is separated from the medium by filtration. The THF is then separated by distillation under vacuum. In this way 130 g of N-[(2,2,2-trichloro-1-amino)-ethyl]-dichloroacetamide are obtained (a yield of 94.7%) in the form of a white solid having a melting point of 132°-133° C.

EXAMPLE 3

Preparation of the compound of the formula:

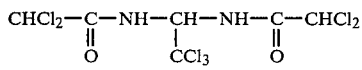

10.2 g of dichloroacetamide (0.08 mole) are dissolved in 150 ml of chloroform. 10 g of triethylamine (0.1 mole) are added. While maintaining the temperature in the neighborhood of 0° C., 23.5 g of N-[1,2,2,2,-tetrachloro)-ethyl]-dichloroacetamide (0.08 mole) dissolved in 150 ml of chloroform are added while stirring in a period of about 1 hour. The temperature is allowed to return to the ambient temperature while stirring, then the product is taken up with 1 liter of water. After decantation, the organic phase is separated and washed twice with 500 ml of water, then dried over magnesium sulphate. The chloroform is distilled off under vacuum and a solid is obtained which is recrystallized from hexane. 24.5 G of N-[(2,2,2-trichloro-1-dichloroacetamido)-ethyl]dichloroacetamide (a yield of 79.5%) having a melting point of 249°-140° C. are thus obtained.

EXAMPLE 4

Preparation of the compound of the formula:

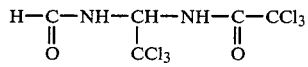

On operating as in Example 1, but replacing the 14.75 g of dichloroacetyl chloride with 18.2 g of trichloroacetyl chloride (0.1 mole), 25.2 g (i.e., a yield of 74.8%) of N-[(2,2,2-trichloro-1-trichloroacetamido)-ethyl]-formamide having a melting point of 157°-158° C. are obtained.

EXAMPLE 5

Preparation of the compound of formula:

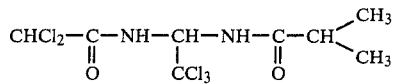

On operating as in Example 3, but replacing the 10.2 g of dichloroacetamide by 6.96 g of isobutyramide (0.08 mole), 21 g (i.e., a yield of 76.3%) of N-[(2,2,2-trichloro-1-dichloroacetamido)-ethyl]-isobutyramide having a melting point of 264°-265° C. are obtained.

EXAMPLE 6

Preparation of the compound of the formula:

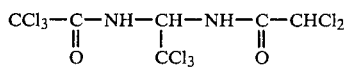

On operating as in Example 1, but replacing the 19.15 g of N-[(2,2,2-trichloro-1-amino)-ethyl]-formamide by 24.7 g of N-[(2,2,2-trichloro-1-amino)-ethyl]-trichloroacetamide (0.08 mole), 21.8 g (i.e., a yield of 65%) are obtained of N-[(2,2,2-trichloro-1-dichloroacetamido)-ethyl]-trichloroacetamide having a melting point of 184°-185° C.

The N-[(2,2,2-trichloro-1-amino-ethyl]-trichloroacetamide used as starting material may be prepared as follows:

300 Ml of THF are saturated with gaseous ammonia and this saturation is maintained during the entire operation. While maintaining the temperature at 0° C., 100 g of N-[(1,2,2,2-tetrachloro)-ethyl]-trichloroacetamide (0.3 mole) are added with stirring over a period of about 1 hour. The precipitate of ammonium chloride which is formed is separated by filtration. The THF is then separated by vacuum distillation. 59 G of N-[(2,2,2-trichloro-1-amino)-ethyl]-trichloroacetamide (i.e., a yield of 62.7%) are thus obtained in the form of a white solid having a melting point of 132°-133° C.

EXAMPLE 7

Preparation of the compound of the formula:

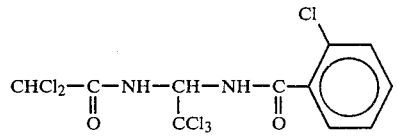

On operating as in Example 1 but replacing the 19.15 g of N-[(2,2,2-trichloro-1-amino)-ethyl]-formamide by 18.2 g of N-[(2,2,2-trichloro-1-amino)-ethyl]-o-chlorobenzamide (0.06 mole) and using 10.3 g of dichloroacetyl chloride (0.07 mole) instead of 14.75 g, after evaporation of the solvent, there are thus obtained 23 g (i.e., a yield of 79.5%) of N-[(2,2,2-trichloro-1-dichloroacetamido)-ethyl]-o-chlorobenzamide having a melting point of 214°-215° C.

The N-[(2,2,2-trichloro-1-amino)-ethyl]-o-chlorobenzamide used as starting material may be prepared as follows:

One operates as for the preparation of the N-[(2,2,2-trichloro-1-amino)-ethyl]-trichloroacetamide with the exception that the 100 g of N-[(1,2,2,2-tetrachloro)-ethyl]-trichloroacetamide are replaced by 100 g of N-[(1,2,2,2-tetrachloro)-ethyl]-o-chlorobenzamide (0.31 mole). 89 g (i.e., a yield of 94.7%) of N-[(2,2,2-trichloro-1-amino)-ethyl]-o-chlorobenzamide are obtained in the form of a white solid having a melting point of 169°–170° C.

EXAMPLE 8

Preparation of the compound of the formula:

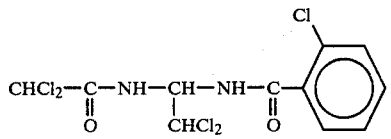

24 g of N-[(2,2-dichloro-1-amino)-ethyl]-dichloroacetamide (0.1 mole) are dissolved in 300 ml of tetrahydrofuran (THF). 10.1 g of treithylamine (0.1 mole) are added. While maintaining the temperature at 20°–15° C., 17.5 g of o-chlorobenzoyl chloride (0.1 mole) dissolved in 50 ml of THF are added with stirring in about 15 minutes. Then the mixture is stirred for 1 hour while allowing it to return to the ambient temperature. The precipitate of triethylamine hydrochloride is filtered off and the THF is separated by vacuum distillation. A brown solid is obtained which is recrystallized from a 50/50 mixture of carbon tetrachloride-hexane. 15.3 g (i.e., a yield of 40.4%) of N-[(2,2-dichloro-1-dichloroacetamido)-ethyl]-o-chlorobenzamide having a melting point of 179°–180° C. are thus obtained.

The N-[(2,2-dichloro-1-amino)-ethyl]-dichloroacetamide used as starting material may be prepared as indicated in Example 14.

EXAMPLE 9

Preparation of the compound of the formula:

CHCl₂—C—NH—CH—NH—C—CH<CH₃/CH₃
  ‖      |      ‖
  O    CHCl₂    O

On operating as in Example 8, but replacing the 17.5 g of o-chlorobenzoyl chloride by 11 g of isobutyryl chloride (0.103 mole), 17.7 g (i.e., a yield of 57.1%) are obtained of N-[(2,2-dichloro-1-isobutyramido)-ethyl]-dichloroacetamide having a melting point of 189°–190° C.

EXAMPLE 10

Preparation of the compound of the formula:

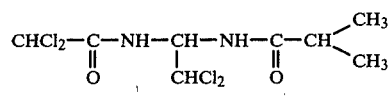

On operating as in Example 8, but replacing the 17.5 g of o-chlorobenzoyl chloride by 10 g of acryloyl chloride (0.11 mole), 12.8 g (i.e., a yield of 43.5%) of N-[(2,2-dichloro-1-acrylamido)ethyl]-dichloroacetamide are thus obtained.

EXAMPLE 11

Preparation of the compound of formula:

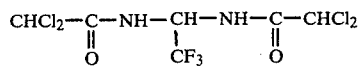

6.4 g of dichloroacetamide (0.05 mole) are dissolved in 50 ml of THF, and 7 g of triethylamine (0.07 mole) are added. The temperature is maintained at 0° C. and 12.3 g of N-[(2,2,2-trifluoro-1-chloro)-ethyl]-dichloroacetamide (0.05 mole) dissolved in 20 ml of THR are added with stirring in about 15 minutes. The mixture is then stirred for three hours while allowing it to return to the ambient temperature. The triethylamine hydrochloride is filtered off and the THF is removed by vacuum distillation. 15 g (i.e., a yield of 89%) are thus obtained of N-[(2,2,2-trifluoro-1-dichloroacetamido)-ethyl]-dichloroacetamide in the form of a brown viscous liquid.

The N-[(2,2,2-trifluoro-1-chloro-ethyl]-dichloroacetamide used as starting material can be prepared as follows:

19.2 g of dichloroacetamide (0.15 mole) are dissolved in 150 ml of benzene and 22 g of fluoral hydrate (0.2 mole) and 1 ml of sulphuric acid are added in a period of about 15 minutes. The mixture is refluxed for 6 hours with stirring. After cooling and filtration, 26.5 g of N-[(2,2,2-trifluoro-1-hydroxy)-ethyl]-dichloroacetamide (i.e., a yield of 78%) are obtained in the form of a white solid having a melting point of 70°–71° C.

5.5 g of N-[(2,2,2-trifluoro-1-hydroxy)-ethyl]-dichloroacetamide (0.025 mole) and 7.5 g of thionyl chloride (0.06 mole) are introduced with stirring into a 100 ml reactor. The mixture is refluxed for 3 hours, then 30 ml of hexane are added in order to facilitate the precipitation during cooling. After filtration, 4.4 g of N-[(2,2,2-trifluoro-1-chloro)-ethyl]-dichloroacetamide (i.e., a yield of 72%), are obtained in the form of a white solid having a melting point of 54°–55° C.

EXAMPLE 12

Preparation of the compound of the formula:

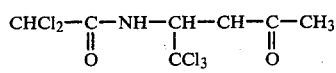

On operating as in Example 1, but replacing the N-[(2,2,2-trichloro-1-amino)-ethyl]-formamide by N-[(2,2,2-trichloro-1-amino)-ethyl]-acetamide, N-[(2,2,2-trichloro-1-dichloroacetamido)ethyl]-acetamide having a melting point of 239°–240° C. is obtained with a yield of 61.5%.

The N-[(2,2,2-trichloro-1-amino)-ethyl]-acetamide used as starting material is prepared by the method used to prepare the N-[(2,2,2-trichloro-1-amino)-ethyl]-trichloroacetamide, but replacing the 100 g of N-[(1,2,2,2-tetrachloro)-ethyl]-trichloroacetamide by 320 g of N-[(1,2,2,2-tetrachloro)-ethyl]-acetamide (1.42 mole). The addition of the THF saturated with ammonis is effected in 1 hour and 45 minutes. 262 g of N-[(2,2,2-trichloro-1-amino)-ethyl]-acetamide (i.e., a yield of 89.6%) are obtained in the form of a white solid having a melting point of 134°–135° C.

EXAMPLE 13

Preparation of the compound of the formula:

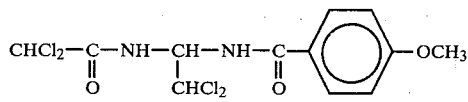

On operating as in Example 8, but replacing the o-chlorobenzoyl chloride by p-methoxybenzoyl chloride, there is obtained, with a yield of 70.9%, N-[(2,2-dichloro-1-dichloroacetamido)ethyl]-p-methoxybenzamide having a melting point of 171°–172° C.

EXAMPLE 14

Preparation of the compound of the formula:

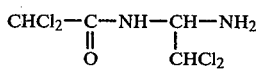

64 g of dichloroacetamide (0.5 mole) are dissolved in 60 ml of benzene and 68 g of dichloroacetaldehyde (0.6 mole) and 1 ml of sulphuric acid are added in about 10 minutes. The mixture is refluxed for 5 hours and the solvent and the excess of dichloroacetalhyde are evaporated under vacuum. 118 g of crude N-[(2,2-dichloro-1-hydroxy)-ethyl]-dichloroacetamide are thus obtained (i.e., a yield of 98%) in the form of a substantially colorless viscous liquid.

| Analysis: | % Cl | % N |
|---|---|---|
| Found | 55.7 | 5.8 |
| Calculated for $C_4H_5NO_2Cl_4$ | 58.9 | 5.8 |

210 g of N-[(2,2-dichloro-1-hydroxy)-ethyl]-dichloroacetamide (0.87 mole) prepared as indicated above and 300 g of thionyl chloride (2.5 moles) are introduced with stirring into a 500 ml reactor. The mixture is refluxed for 2 hours and 30 minutes. 300 ml of hexane are added in order to facilitate precipitation during cooling. After filtration, 175 g of N-[(2,2,1-trichloro)-ethyl]-dichloroacetamide are obtained (i.e., a yield of 77.5%), in the form of a white solid having a melting point of 77°–78° C.

600 ml of THF are saturated with gaseous ammonia and this saturation is maintained during the entire following operation. While maintaining the temperature at 0° C., 130 g of N-[(2,2,1-trichloro)-ethyl]-dichloroacetamide (0.5 mole) prepared as indicated above, are added with stirring in about 1 hour. The ammonium chloride formed is separated by filtration. The THF is then evaporated under vacuum. 95.4 g of N-[(2,2-dichloro-1-amino)-ethyl]dichloroacetamide are thus obtained (i.e., a yield of 79.5%) in the form of a white solid having a melting point of 96°–97° C.

EXAMPLE 15

Preparation of compound of formula:

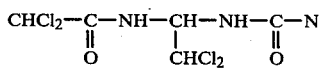

On operating as in Example 3, but replacing the dichloroacetamide and the N-[(1,2,2,2-tetrachloro)-ethyl]-dichloroacetamide by formamide and N-[(1,2,2-trichloro)-ethyl]-dichloroacetamide, respectively, N-[(2,2-dichloro-1-dichloroacetamido)-ethyl]formamide having a melting point of 79°–80° C. is obtained with a yield of 74.6%.

EXAMPLE 16

Preparation of the compound of the formula:

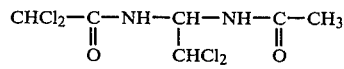

On operating as in Example 3, but replacing the dichloroacetamide and the N-[(1,2,2,2-tetrachloro)-ethyl]-dichloroacetamide by acetamide and N-[(1,2,2-trichloro)-ethyl]-dichloroacetamide, respectively, N-[(2,2-dichloro-1-dichloroacetamido)-ethyl]acetamide having a melting point of 63°–64° C., is obtained with a yield of 78%.

EXAMPLE 17

Antidote activity of the compounds according to the invention.

A soil, consisting of two parts by weight of clay and three parts by weight of sand, is placed in small plastic troughs having the dimensions 18×12×5 cm. On this soil are sown, along 4 furrows of 0.5 cm in depth, 10 seeds of maize, variety "Sandrina", and 10 seeds of barley, variety "Rika".

The sowings thus made are separated into 3 lots, each lot containing 5 small troughs. On the first lot is spread a layer 2 cm in thickness of a soil having undergone no treatment. On the second lot is spread a layer 2 cm in thickness of a soil in which has been incorporated by careful mixing a herbicide naturally phytotoxic for the maize at the dose used. Finally, on the third lot is spread a layer 2 cm in thickness of a soil in which has been incorporated the same herbicide as for the second lot, at the same dose and an antidote product according to the invention.

For their incoroporation in the soil the herbicide and the antidote are formulated in the form of aqueous suspensions. The amounts of herbicide used correspond to doses of herbicide of 5 kg and 10 kg/ha. The amounts of antidote product used correspond to doses equal to one-tenth of the doses of the herbicide, i.e., 0.5 and 1 kg/ha. The herbicide used is E.P.T.C. or ethyl N,N-dipropyl thiolcarbamate. The antidote products tested are the compounds of Examples 1 to 15.

The batches of troughs, once treated, are placed in a greenhouse maintained at 20° C. and at a relative humidity of 70%. 12 and 20 days after the treatment (J+12; J+20), the lots are examined; on the one hand the herbicidal efficiency of the association "antidote+-herbicide" is determined and on the other hand, the antidote efficiency of the compound according to the invention tested is determined. The antidote efficiency E is evaluated by measuring the average height of the maize plants in the three lots. It is given by the formula:

$$E = \frac{(C - B) \times 100}{(A - B)}$$

in which A denotes the average size of the maize plants in the untreated control lots, B is the average size of the maize plants in the lots treated with the herbicide alone and C is the average size of the maize plants in the lots treated with the herbicide and the antidote. An antidote efficiency equal to 0 then corresponds to C=B and an antidote efficiency equal to 100 corresponds to C=A.

It is found that in all the tests carried out with the "antidote+herbicide" associations with a weak dose or a strong dose, the barley, which serves here as weeds of reference, is destroyed to 100%, which proves that the herbicidal efficiency towards the Graminae is not reduced by the products according to the invention.

The results relating to the antidote efficiency E are tabulated in the following Table 1.

It is seen that the compounds of Examples 1, 3, 4, 9, 11 and 14, associated with E.P.T.C., have a particularly marked antidote efficiency.

TABLE 1

| Compound of Example | ANTIDOTE EFFICIENCY | | | |
|---|---|---|---|---|
| | Date of Examination | | | |
| | Doses kg/ha Herbicide & Antidote | | | |
| | 5.0 + 0.5 | 10.0 + 1.0 | 5.0 + 0.5 | 10.0 + 1.0 |
| 1 | 55 | 91 | 98 | 98 |
| 2 | 66 | 47 | 71 | 40 |
| 3 | 105 | 93 | 98 | 86 |
| 4 | — | — | 93 | 88 |
| 5 | 33 | 56 | 29 | 22 |
| 6 | 65 | 25 | 37 | 18 |
| 7 | 68 | 15 | 55 | 22 |
| 8 | — | — | 5 | 55 |
| 9 | 120 | 69 | 86 | 81 |
| 10 | 36 | 49 | 36 | 45 |
| 11 | 100 | 94 | 104 | 90 |
| 12 | 23 | 24 | 11 | 22 |
| 13 | — | — | — | 32 |
| 14 | 79 | 68 | 94 | 78 |

TABLE 1-continued

| Compound of Example | ANTIDOTE EFFICIENCY | | | |
|---|---|---|---|---|
| | Date of Examination | | | |
| | Doses kg/ha Herbicide & Antidote | | | |
| | 5.0 + 0.5 | 10.0 + 1.0 | 5.0 + 0.5 | 10.0 + 1.0 |
| 15 | 1 | 25 | 0.15 | 17 |

What is claimed is:

1. A composition containing 0.9% to 50% by weight of an antidote product and 1% to 90% by weight of a herbicide belonging to the families of chloroacetanilides, ureas, triazines, carbamates, uracils or thiolcarbamates, the ratio by weight $$\frac{\text{antidote product}}{\text{herbicide}}$$

being between 0.001 and 10 and the complement to 100% being constituted by inert additives, in which the antidote product is a member selected from the group consisting of N-[(2,2-dichloro-1-isobutyramido)-ethyl]-dichloroacetamide, N-[(2,2,2-trifluoro-1-dichloroacetamido)-ethyl]-dichloroacetamide and N-[(2,2-dichloro-1-amino)-ethyl]-dichloroacetamide.

2. A composition according to claim 1 in which the herbicide belongs to the thiolcarbamate family.

3. A composition according to claim 2 in which the herbicide is ethyl N,N-dipropyl-thiolcarbamate.

4. A composition according to claim 1, 2 or 3 in which the antidote product is N-[(2,2-dichloro-1-isobutyramido)-ethyl].

5. A composition according to claim 1, 2 or 3 in which the antidote product is N-[(2,2,2-trifluoro-1-dichloroacetamido)ethyl]-dichloroacetamide.

6. A composition according to claim 1, 2 or 3 in which the antidote product is N-[(2,2-dichloro-1-amino)-ethyl]-dichloroacetamide.

* * * * *